(12) United States Patent
Lubatschowski et al.

(10) Patent No.: US 8,221,400 B2
(45) Date of Patent: Jul. 17, 2012

(54) APPARATUS FOR AND METHOD OF REFRACTIVE SURGERY WITH LASER PULSES

(75) Inventors: Holger Lubatschowski, Gehrden (DE); Christian Rathjen, Bremen (DE)

(73) Assignee: SIE Surgical Instruments Engineering AG, Port (CH)

( * ) Notice: Subject to any disclaimer, the term of this patent is extended or adjusted under 35 U.S.C. 154(b) by 1766 days.

(21) Appl. No.: 11/207,776

(22) Filed: Aug. 22, 2005

(65) Prior Publication Data

US 2007/0055221 A1    Mar. 8, 2007

(51) Int. Cl.
*A61B 18/18* (2006.01)

(52) U.S. Cl. .................. 606/5; 606/2; 606/4; 128/898

(58) Field of Classification Search .......... None
See application file for complete search history.

(56) References Cited

U.S. PATENT DOCUMENTS

| | | | |
|---|---|---|---|
| 3,527,198 A | 9/1970 | Takaoka | |
| 5,312,396 A * | 5/1994 | Feld et al. | 606/11 |
| 5,785,704 A | 7/1998 | Bille et al. | |
| 5,786,560 A | 7/1998 | Tatah et al. | |
| 5,882,572 A | 3/1999 | Lutze et al. | |
| 5,928,221 A * | 7/1999 | Sasnett et al. | 606/5 |
| 5,993,441 A * | 11/1999 | Muller et al. | 606/10 |
| 6,293,938 B1 * | 9/2001 | Muller et al. | 606/5 |
| 6,509,547 B1 | 1/2003 | Bernstein et al. | |
| 6,592,574 B1 * | 7/2003 | Shimmick et al. | 606/4 |
| 6,787,733 B2 | 9/2004 | Lubatschowski et al. | |
| 7,621,637 B2 | 11/2009 | Rathjen et al. | |
| 2001/0035447 A1 | 11/2001 | Gartner | |
| 2003/0110862 A1 * | 6/2003 | Lubatschowski et al. | 73/644 |
| 2004/0002199 A1 | 1/2004 | Fukuyo | |
| 2004/0243111 A1 * | 12/2004 | Bendett et al. | 606/5 |
| 2005/0110948 A1 | 5/2005 | Bille | |
| 2006/0195076 A1 | 8/2006 | Blumenkranz | |
| 2009/0048586 A1 | 2/2009 | Krueger | |
| 2009/0294422 A1 | 12/2009 | Lubatschowski | |

FOREIGN PATENT DOCUMENTS

| | | |
|---|---|---|
| GB | 2218660 | 11/1989 |
| WO | 2007/022948 | 3/2007 |
| WO | 2007/124602 | 11/2007 |
| WO | 2009023774 | 2/2009 |
| WO | 2009/090095 | 7/2009 |

* cited by examiner

*Primary Examiner* — Henry M Johnson, III
*Assistant Examiner* — Lynsey Crandall
(74) *Attorney, Agent, or Firm* — Roylance, Abrams, Berdo & Goodman, L.L.P.

(57) ABSTRACT

A method and apparatus for a refractive surgical treatment that uses a laser which produces a succession of laser pulses applied to a material region. The laser pulses irradicates the material region to be divided where the energy of the individual pulse in less than the energy required to produce the material division or cutting.

18 Claims, 3 Drawing Sheets

Fig. 5

APPARATUS FOR AND METHOD OF REFRACTIVE SURGERY WITH LASER PULSES

FIELD OF THE INVENTION

The invention concerns a method of refractive surgical treatment by means of a laser, in which a succession of laser pulses is produced and a material region to be divided is irradiated with the succession of laser pulses. A further aspect of the invention is an apparatus for refractive surgical treatment including
  means for producing a succession of laser pulses, and
  means for guiding the laser pulses on to a material region to be divided.

BACKGROUND OF THE INVENTION

The use of laser pulses, in particular ultrashort laser pulses with a laser pulse duration in the range of between approximately $10^{-15}$ s and $5\times10^{-10}$ s for the purposes of high-precision laser microstructuring operations is known.

G Mourou, in U.S. Pat. No. 5,656,186 (EP 0 754 103 B1, application filing date 8.4.94 'Method for controlling configuration of laser induced breakdown and ablation'), describes the basic suitability of individual ultrashort laser pulses for material processing.

In his dissertation relating to 'Mikromaterialbearbeitung mit ultrakurzen Laserpulsen', Cuvillier Verlag Göttingen, 1999, S Nolte discusses aspects of material processing using femtosecond laser pulses.

The treatment of vision defects in the human or animal eye by means of short laser pulse treatment is also previously known.

Thus in U.S. Ser. No. 005984916A (application filing date 20.4.93, 'Ophthalmic surgical laser and method') Shui T Lai describes the advantages of ultrashort pulses for refractive surgery on the eye.

In an article relating to 'Application of ultrashort laser pulses for intrastromal refractive surgery', Graefe's Arch Clin Exp Ophthalmol 238:33-39, 2000, H Lubatschowski et al describe the use of laser systems which produce ultrashort laser pulses of a duration of 100-200 femtoseconds, in the area of intrastromal refractive surgery.

Kurtz et al, 'Optimal Laser Parameters for Intrastromal Corneal Surgery', SPIE, Vol 3255, 56-66, January 1998, also use ultrashort laser pulses for tissue treatment.

For the treatment of vision defects, for example short-sightedness (myopia), various surgical interventions on the eye are employed to correct or at least reduce such defective vision. For example, in a first surgical treatment method (referred to as the 'LASIK' method), in a first step a cut is made with a special mechanical cutting device along a frontal plane through the cornea in order in that way to be able to lift off a flap of the cornea and fold it back.

Subsequently in a second step, usually starting from the cut surface of the body of the eye, a material removal operation is carried out in order to remove a lens-shaped piece of tissue. That material removal operation is either executed with the same mechanical cutting device as the first step in order to cut out the piece of tissue. In another operative procedure a second step involves material ablation by means of an excimer laser, which does not involve a cut but material vaporisation.

Then in a third step the corneal flap which had been folded away is folded back into place again and thus with its cut surface joins the surface produced by the lens-shaped cuffed-out configuration/the lens-shaped removal. The two wound surfaces are then joined together as they heal.

The optical properties of the cornea are changed by removal of the lens-shaped piece of tissue from the cornea. It is possible to achieve specifically targeted optical correction by virtue of a specific contour in respect of that lens-shaped piece of tissue.

In another procedure for treating vision defects the lens of the eye is removed and replaced by an artificial lens affording different optical properties. For that purpose it is also necessary in a first step to make an incision in the cornea of the eye in order to permit removal of the lens and fitment of the artificial lens.

Basically mechanical operating instruments are used for the first step in both of the above-mentioned methods as such instruments ensure an acceptable level of cutting performance and precision. The use of known laser cutting methods on the eye is limited as the cut surface quality is frequently not sufficiently high for the optical demands and the healing process is slowed down by virtue of thermal damage in the adjoining region of the cut surface or indeed complications can arise in regard to definitive healing of the operative incisions.

In general, that is to say also in accordance with the present invention, ultrashort laser pulses can be used for cutting, removing and structuring material (for example biological tissue) and for modifying material properties (for example for modifying the refractive index in glass).

The particular advantages of material processing with ultrashort laser pulses (fs-laser pulses) are found in particular in relation to the extremely precise cutting and/or ablation of materials, involving less damage both thermally and also mechanically, than in a series of other material processing methods. Due to focusing of the ultrashort laser pulses, energy is deposited at the focus in a very limited space by triggering of a microplasma and a cutting effect or material ablation is achieved by so-called photodisruption. It is possible to achieve removal rates in the sub-μm range with cutting widths of less than 500 nm. By virtue of a non-linear interaction mechanism involved in photodisruption, material removal is in that case substantially independent of the properties of the material. In particular, when using fs-laser pulses, it is also possible to deal with materials involving a high level of thermal conductivity (such as for example metals) and materials involving a low degree of laser light absorption (such as for example polymers or certain biological tissues).

As an alternative to ablation on the surface of a material to be treated, focusing into materials which are transparent for laser radiation (such as for example the cornea of an eye) also makes it possible to achieve a cutting effect in the interior of the transparent material (tissue).

One problem in material processing by means of laser is that material division is achieved by the laser energy in the irradiated region and in addition material changes are caused in adjoining regions, and such changes are generally undesirable. Those changes in material are decisively dependent in extent and magnitude on how high the energy of the laser beam and its temporal distribution is.

EP 1 284 839 A1 and U.S. Pat. No. 6,787,733 W2 describe a method of laser processing of materials, involving online control of the processing result in order to optimise material processing and to minimise unwanted side-effects. Admittedly, online control of the processing operation is possible with that method and in that case also any side-effects which occur can be observed, but it is not possible with that method to avoid surrounding regions of material being influenced by the laser radiation, besides the region which is to be treated thereby.

The interaction mechanism in tissue treatment by means of short intensive laser pulses is based on so-called photodisruption. Photodisruption occurs when light is focused to intensities of the order of magnitude of $10^{11}$ to $10^{12}$ W/cm². At such high levels of intensity, almost any kind of material is abruptly ionised by virtue of multi-photon absorption (plasma generation). If that process takes place in transparent material (water, glass, cornea) it is referred to as 'optical' breakdown.

The explosive expansion of the laser-induced plasma causes the development of a strong pressure front and—if the process takes place in a fluid environment—a cavitation bubble. The pressure front as well as the cavitation bubbles can represent a considerable mechanical damage potential for surrounding material/tissue. That damage potential of an individual laser pulse scales however with the laser pulse energy.

A high level of intensity however is necessary to trigger optical breakdown. The shorter a laser pulse, the correspondingly less energy it transports, at the same level of intensity. Consequently, short laser pulses are a necessary prerequisite in order to implement photodisruption at a high level of precision and with slight mechanical side-effects.

The laser pulse duration, that is to say the time for which the laser radiation acts, is however also of crucial significance in regard to thermal damage to the irradiated material. If the radiation duration of the laser is so short that, during the irradiation procedure, no significant amount of thermal energy is lost due to heat diffusion from the absorption volume, that situation is referred to as 'thermal confinement'. The maximum irradiation time (laser pulse duration) at which the conditions of 'thermal confinement' are maintained is also referred to as the thermal relaxation time $\tau_R$ and is given by the following relationship:

$$\tau_R = \frac{\delta^2}{4\kappa}$$

In that relationship:

δ: denotes the optical depth of penetration into the irradiated material/tissue, in the case of disruption in transparent media δ corresponds to the expansion in the non-linear absorption zone; and κ: denotes the thermal diffusion constant of the irradiated material/tissue.

If the time of action (laser pulse duration) is markedly shorter than $\tau_R$, the zone of thermal influence which the laser pulse exerts on the irradiated material is determined primarily by the optical depth of penetration δ. In the case of a laser pulse duration which is markedly longer than $\tau_R$, the zone of thermal influence acts beyond the optical depth of penetration by virtue of thermal diffusion.

When dealing with metals in respect of which an optical depth of penetration of only a few nanometers is involved and a comparatively high level of thermal diffusion prevails the use of pico- or even femtoseconds is therefore essential in order also to minimise the zone of thermal influence. Organic substances or biological tissue with a substantially lower level of thermal diffusion and with very much higher optical depths of penetration in contrast have thermal relaxation times in the region of nanoseconds or even microseconds.

However the reduction in the laser pulse duration is subject to technological limits at the present time and also does not prevent the surrounding regions being subjected to unwanted influences.

In principle to achieve material division it is necessary to introduce a certain amount of energy into the region to be divided, with the laser pulse. The level of that energy is dependent on the material. In the case of material division along a line or a surface, a plurality of laser pulses are used in mutually juxtaposed relationship, with the appropriate laser pulse energy, in order to achieve a division line or division surface. The disruptive effect of the individual laser pulses can give rise to unwanted mechanical changes in the material, depending on the respective nature of the material. Such changes include tearing effects in the tissue, which causes an irregular cut surface, or the formation of gas bubbles which can also detrimentally influence the geometry of the cut. In that case the extent of the unwanted changes in the material scales with the energy of the individual laser pulses.

By virtue of the versatile possible forms of use and the possibility of incisions which are controlled in an automated mode, lasers are already used for a series of incision procedures and removal procedures on the eye. A limitation in terms of possible forms of use is however imposed for example due to thermal tissue damage and the in part still unsatisfactory quality of the cut surface. There is therefore a need for improvement to the effect that the cleanness of the cut is increased, that is to say the degree of roughness of the cut surface is reduced and the evenness thereof is enhanced. There is also a need to provide a precise cutting method for refractive surgery, which allows the tissue surrounding the cut surface to be dealt with as gently and carefully as possible. The aim of the invention is to meet that need.

In a German patent application which has not yet been laid open, Lubatschowski describes a method of material and tissue division by means of irradiation of a region of the material with a succession of laser pulses, in which the laser pulse energy of an individual laser pulse of the succession of laser pulses is less than the laser pulse energy which is used to produce material division with an isolated laser pulse in the region irradiated with the individual laser pulse of the succession of laser pulses. That method is suitable for precision cutting of materials with laser pulses.

The merit of the inventor of this patent application is to recognise the advantageous use of that method for refractive surgery. In refractive surgery a deliberate cut is made in the corneal tissue of a human being or animal in order in that way to be able to correct a vision defect. Actual correction of the vision defect is effected in the case of the surgical treatment methods referred to hereinbefore by way of example, by cutting out in a lens form a part of the cornea or by removal and replacement of the lens. There is a need for treatment methods with which such a treatment can be carried out as gently and carefully as possible for the surrounding tissue and at the same time safely and effectively.

SUMMARY OF THE INVENTION

In accordance with the invention that need is met by a method of the kind set forth in the opening part of this specification, in which the laser pulse energy of an individual laser pulse of the succession of laser pulses is less than the laser pulse energy which is required for producing material division with an isolated laser pulse in the region irradiated with the individual laser pulse of the succession of laser pulses.

The invention capitalises on the realisation that, for cutting the cornea, it is not necessarily required for the total energy necessary for the division operation to be introduced at one location with an individual laser pulse. Instead that total energy can be applied by a plurality of laser pulses which are produced for example by one and the same laser and which are successively introduced at the same location in the division region. In that way it is possible to achieve material treatment by means of a plurality of successive laser pulses involving a low level of laser pulse energy and in that case to avoid damage to the irradiated material in the surrounding region.

It has been found that the energy for material division, that is to say that total energy which is at least required to achieve material division, falls with a rising repetition frequency. Consequently with high repetition rates material division can be achieved with a substantially lower level of laser pulse energy than when low repetition rates are used.

The invention provides a treatment method which is suitable both for effecting the first cut in the cornea of the eye with a pulsed laser and also for other incisions in the cornea, for example for cutting out a lens-shaped piece of tissue from the previously produced cut surface. The thermal and mechanical damage to the surrounding tissue is reduced and the quality of the cut surface is increased.

In particular the laser pulse energy can be reduced by reducing the laser pulse intensity and/or the laser pulse duration. This means that the laser pulse intensity and/or the laser pulse duration in the method according to the invention is lower than the laser pulse intensity and/or the laser pulse duration which is required in conventional technology to achieve tissue division. It is possible in that fashion to achieve a reduction in laser pulse energy in a simple manner.

It is particularly advantageous if the irradiated region is spatially overlapped by two or more laser pulses, which occur in succession in respect of time, of the succession of laser pulses. By virtue of that spatial overlap, the laser pulse energy of two or more laser pulses is introduced into the overlap region and thus when added can afford a total energy which achieves material division. That realisation is a departure from the previous approach of spacing the laser pulses from each other as far as possible in respect of time and space in order to separate the thermal influence of each individual laser pulse from that of a subsequent laser pulse, and it achieves a reduction in the unwanted mechanical and thermal influence by virtue of the overlap, insofar as at the same time the laser pulse energy of each individual laser pulse is reduced.

In that respect it is particularly advantageous if the irradiated region is spatially overlapped by two or more laser pulses, which occur in succession in respect of time, of the succession of laser pulses at 100% or in the range of between 10% and 100%, preferably around 70% to 99%, in particular 92%-99%. The overlap of the laser pulses basically depends on the diameter of the laser beam at the focus (focus beam diameter), the laser pulse repetition frequency and the relative advance speed between the material to be cut and the laser. The overlap in percent is defined in this connection as:

$$\text{Overlap} = 100 \times \left(1 - \frac{\text{advance speed}}{\text{laser pulse repetition frequency} \times \text{focus beam diameter}}\right)$$

The specified values are suitable for material division of a large number of different materials. The spatial overlap of 100% can be for example of such a nature that two or more laser pulses 100% overlap, thereupon the laser beam is displaced relative to the material being worked and then once again two or more laser pulses are discharged, which 100% overlap. As an alternative to that discontinuous advance, it is advantageous in many uses if a continuous advance movement takes place and if the movement is so adjusted that, with a given laser pulse repetition frequency and laser beam diameter at the focus, an overlap of 70-99%, in particular 92%-99%, is achieved.

It is further advantageous if the laser pulse energy, the laser pulse intensity, the dimensions of the focus area, the laser pulse duration of an individual laser pulse, the laser pulse repetition frequency of the succession of laser pulses and/or the advance speed between the laser beam and the material to be processed is preset in dependence on the properties of the material. An important dimension of the focus area, which is to be preset, is frequently for example the diameter of the laser beam at the focus or the length of the focus area in the beam direction, which is influenced inter alia by the aperture. The optimum parameters depend on the properties of the material to be processed, in particular the thermal diffusion constant and the relaxation time of the material. In principle it is for example advantageous to set higher laser pulse repetition frequencies, when high thermal diffusion constants are involved, than when low thermal diffusion constants are employed. There is an inverse relationship between relaxation time and laser pulse repetition frequency: with long relaxation times, usually lower laser pulse repetition frequencies can be selected than when the relaxation times are short.

It is further advantageous if the laser pulse repetition frequency of the succession of laser pulses is so high that, within a material-specific duration of the material to be divided, for example the thermal relaxation time, at least two laser pulses are delivered on to the material to be divided. In that way the laser pulse energy of the two laser pulses delivered within the material-specific period can be accumulated and cause division of the material. In that case the thermal and mechanical damage can be reduced by a large number of laser pulses being delivered on to a region of the material to be divided, within the material-specific period, and by the energy of each of those laser pulses being selected at a suitably low level in order to introduce the total accumulated energy required for material division, precisely by means of that large number of laser pulses.

It has proven to be particularly advantageous in this respect if the laser pulse repetition frequency is greater than 10 Hz, in particular greater than 50 Hz and is preferably between 100 Hz and 50 MHz. Those laser pulse repetition frequency ranges already cause a marked reduction in the required laser pulse energy per laser beam and can thus significantly reduce the mechanical damage.

With the above-mentioned embodiments, it is particularly to be noted that there is a mathematical relationship between overlap, laser pulse repetition frequency, the dimensions of the focus area, for example the diameter of the laser beam at the focus, and the advance speed. The ultimately decisive parameter, that is to say the number of laser pulses introduced at a material processing location or the overlap, can be influenced by a variation in the corresponding other parameters. Thus that number can be individually increased in each case by reducing the advance speed, increasing the diameter of the laser beam at the focus or increasing the laser pulse repetition frequency, if the corresponding two other parameters are kept constant. A reduction in the diameter of the laser beam at the focus, an increase in the advance speed and a reduction in the laser pulse repetition frequency make it possible to achieve a reduction in the number of laser pulses per location point on the line along which material processing is effected.

In addition it is advantageous if the laser pulse energy, the laser pulse intensity, the dimensions of the focus area, the laser pulse duration of an individual laser pulse, the laser pulse repetition frequency of the succession of laser pulses and/or the advance speed between the laser beam and the material to be processed is changed during the processing operation. With that embodiment it is for example possible to set the laser pulse energy of the individual laser pulses in such a way that, in dependence on the overlap of the laser pulses, precisely the energy required for material division at the location just being processed is introduced into the material. In that respect it may be advantageous if the laser pulse energy is set in dependence on the predetermined or set laser pulse repetition frequency and/or advance speed. Such setting can be effected automatically or manually by the user.

In the case of developments of the method involving an adjustable laser pulse repetition frequency and an adjustable laser pulse energy, it is particularly advantageous if a first laser pulse energy is set in the case of a first laser pulse repetition frequency and a second laser pulse energy which is lower than the first laser pulse energy is set in the case of a second laser pulse repetition frequency which is higher than the first laser pulse repetition frequency. That provides for automatic adaptation of the laser pulse energy to the laser pulse repetition frequency and in that respect in each case the required accumulated total energy for achieving material division is introduced.

In that respect it is particularly advantageous if
the laser pulse repetition frequency is set automatically in dependence on the laser pulse energy, or
the laser pulse energy is set automatically in dependence on the laser pulse repetition frequency,
the laser pulse energy and/or the laser pulse repetition frequency are set automatically in dependence on the advance speed, or
the laser pulse repetition frequency, the laser pulse energy and/or the advance speed are set automatically in dependence on at least one material property of the material to be divided.

This development in the method permits the method parameters which are primarily crucial for material division to be set in dependence on each other or to be automatically correctly set in dependence on the material to be processed. Thus, in the case of the method according to the invention, it is possible to have recourse to a database which provides the ideal method parameters for respectively typical materials and those method parameters are then set by material selection. Alternatively, the total energy required for material division can be taken from a database and then, on the basis of method parameters selected by the user, the correspondingly other method parameters are so selected that that required total energy is achieved.

A further aspect of the invention lies in a method of the kind set forth in the opening part of this specification or the kind referred to above, wherein, in the start region of the dividing operation, the total energy introduced at a location of the material to be processed is higher than in a region in the further course of the dividing operation.

That development is based on the realisation that, to achieve initial material division in a material, a higher level of total energy is required in order to achieve a first material division effect and subsequently a lower level of total energy is required for maintaining and enlarging that initial material division effect. It is therefore advantageous for the laser pulse energy, after an initially high level in the start region of the dividing operation to achieve initial material division, to be subsequently reduced to a lower level which is sufficient to maintain and continue with the initial material division effect in order in that way to minimise damage along the division line or the division surface.

In particular it is advantageous if, in the start region, the laser pulse energy, the laser pulse repetition frequency and/or the number of laser pulses delivered on to a location on the material is higher and/or the advance speed between the laser beam and the material to be processed is lower than in the further course of the dividing operation. The laser pulse energy is composed of the laser pulse intensity and the laser pulse duration. Therefore, to achieve an initial dividing operation in the start region, it is possible to set a higher level of laser pulse intensity than in the region of the further course of the dividing operation, for maintaining and continuing with the division effect.

In the same manner, with a constant laser pulse intensity, the laser pulse duration could be increased in the start region and reduced in the further course of the procedure and/or the laser pulse repetition frequency could be increased in the start region and reduced in the further course of the procedure.

A further development provides that the laser pulse intensity and/or the laser pulse duration of an individual laser pulse is higher in the start region of the dividing operation than in a region in the further course of the dividing operation. That development can in the same manner implement initial division with a high level of laser pulse energy and further division with a lower level of laser pulse energy, but with a variation in other parameters than in the above-described embodiment.

In particular, for the method according to the invention, it is advantageous if the laser pulse duration is less than ten picosecond, and in particular less than one picosecond. The laser beam treatment which is achieved in that way, in the femtosecond range, permits particularly advantageous laser pulse energy rates and laser pulse repetition frequencies, for a large number of materials, and generally avoids unwanted damage.

It is further advantageous for the method according to the invention if the laser beam is focused, preferably with an optical system having a numerical aperture which is at least so large that material division is achieved beneath the surface of a semi-transparent or completely transparent material without regions of material which are above or beneath the division region being damaged. That makes it possible to produce a laser beam focus and, upstream and downstream of that laser beam focus in the direction of the beam, to avoid division of or damage to the material, whereas such a material division effect is achieved at the laser beam focus.

Finally it is further advantageous for the method according to the invention if the dividing operation is observed and, if the division performance drops off, the total energy introduced is increased by modifying one of the parameters which are relevant in terms of division performance, as set forth hereinbefore. In this connection the term observation is intended to denote direct optical or sensor observation of the cut or also observation or monitoring of technical parameters, for example equipment performance data, by a user or automatically, in order to infer an altered division performance from a change in those parameters.

The method can be used in particular to perform a first cut for opening up the cornea by irradiating a region of the cornea with the succession of laser pulses. That first cut can either only partially open up the cornea in order for example to apply the LASIK operative technique or the first cut can completely cut through the cornea in order to afford access to the lens.

It is further preferred if a second cut for removal of a lens-shaped piece of tissue from the cornea is implemented by irradiating a region of the cornea with the succession of laser pulses.

The first and second cuts are performed in the state of the art in the form of planar cuts. The method according to the invention makes it possible for the first time to achieve a precise geometry in respect of the cut surface, which can be geometrically freely selected by the surgeon, by means of laser division. In addition the method provides a high surface quality for the cut surfaces as well as a low level of thermal and mechanical damage to the tissue adjacent to the cut surfaces. The laser cutting technique which is possible by the method according to the invention, for cutting out a lens-shaped piece of tissue, permits an incision to be made with more precision than when using a mechanical cutting technique which, in the state of the art, is always performed as a planar cut on a deliberately (elastically) deformed portion of cornea (referred to as applanation).

A further aspect of the invention is an apparatus of the kind set forth in the opening part of this specification, which is developed in accordance with the invention in that the means for producing a succession of laser pulses are so adapted that the laser pulse energy of an individual laser pulse of the succession of the laser pulses is less than the laser pulse energy which is required for producing material division with an isolated laser pulse in the region irradiated with the individual laser pulse of the succession of laser pulses. In that way it is possible to keep the laser pulse energy of an individual laser pulse in a low range and thereby to achieve material division with the method according to the invention. In regard to the advantages and effects of the apparatus designed in that way attention is directed to the foregoing description of the corresponding method.

A development of the apparatus according to the invention can provide that the means for producing the succession of laser pulses is adapted to reduce the laser pulse energy by a reduction in the laser pulse intensity and/or the laser pulse duration.

A further development of the apparatus according to the invention can include advance means for producing a relative movement between the laser beam and the material to be divided and means for producing a laser pulse repetition frequency, which co-operate in such a way that the irradiated region is spatially overlapped by two laser pulses, which occur in succession in respect of time, of the succession of laser pulses. That achieves the overlap, which is advantageous in accordance with the invention, of at least two successive laser pulses. In that case the advance means are preferably so designed that they are operable in dependence on the laser pulse repetition frequency.

It is further advantageous if the advance means and the means for producing a laser pulse repetition frequency co-operate in such a way that the irradiated region is spatially overlapped by two laser pulses, which occur in succession in respect of time, of the succession of laser pulses at 100% or in the range of between 10% and 100%, preferably around 70% to 99%, preferably from 92% to 99%. In that respect attention is directed to the preceding description of the corresponding form of the method.

Preferably, the apparatus according to the invention has control means for setting the laser pulse energy, the laser pulse intensity and/or the laser pulse duration of an individual laser pulse, the laser pulse repetition frequency of the succession of laser pulses, the dimensions of the focus area of the laser beam at the processing location, for example the diameter of the laser beam at the focus and/or the advance speed between the laser beam and the material to be processed, in dependence on the material properties. The control means can be actuated automatically by the apparatus in respect of one of the parameters in dependence on other parameters or can be actuated manually by a user.

In that respect it is particularly advantageous if the control means are so adapted that the laser pulse repetition frequency of the succession of laser pulses is so high that, within a material-specific period of time, for example the thermal relaxation time of the material to be divided, at least two laser pulses are delivered to the material to be divided. That achieves the advantageous accumulation of two or more laser pulses within the material-specific period of time and in that way attains particularly gentle and careful division of the material.

In particular in that case the control means can be so adapted that the laser pulse repetition frequency is greater than 10 Hz, in particular greater than 50 Hz and preferably between 100 Hz and 50 MHz. In that respect attention is directed to the foregoing corresponding form of the method.

It is further advantageous if the control means are adapted to alter at least one of the six above-listed parameters during the processing operation. In that way the total energy and/or the laser pulse energy can be set in dependence on the material properties or in dependence on other parameters of the cutting operation.

The control means can preferably be so adapted that
  the laser pulse repetition frequency is set automatically in dependence on the laser pulse energy, or
  the laser pulse energy is set automatically in dependence on the laser pulse repetition frequency,
  the laser pulse energy and/or the laser pulse repetition frequency are set automatically in dependence on the advance speed, or
  the laser pulse repetition frequency, the laser pulse energy and/or the advance speed are set automatically in dependence on the at least one material property of the material to be divided.

In particular it is advantageous for the apparatus according to the invention if the control means are adapted to control at least one of the six above-listed parameters (laser pulse repetition frequency, laser pulse energy, laser pulse intensity, laser pulse duration, focus dimension and advance speed) in such a way that in the start region of the division operation the total energy introduced into a location of the material to be processed is higher than in a region in the further course of the division operation.

It is further preferred in a development of the apparatus according to the invention that the control means are adapted in the start region to set the laser pulse energy, the laser pulse repetition frequency and/or the number of laser pulses delivered to a location of the material higher and/or the advance speed between the laser beam and the material to be processed lower than in the further course of the division operation.

Preferably the control means are adapted to set the laser pulse intensity and/or the laser pulse energy of an individual laser pulse higher in the start region of the division operation than in the further course of the division operation.

In particular it is advantageous if the means for producing a succession of laser pulses are adapted to produce a laser pulse duration of less than 10 picoseconds, preferably less than 1 picosecond.

The apparatus according to the invention can be further developed by focusing means for focusing the laser beam, preferably with an optical system with a numerical aperture which is at least so great that material division is achieved under the surface of a semitransparent or completely transparent material without material regions above or below the division region being damaged.

Finally a further development of the apparatus according to the invention provides an observation device for observing the division operation, which co-operates with the means for producing a succession of laser pulses, the means for guiding the laser pulses on to a material region to be divided and/or the advance means in such a way that if the division performance drops off the total energy introduced is increased by altering at least one of the six above-listed parameters. In this respect attention is directed to the preceding description relating to the method involving observation of the division operation.

In regard to the developments of the apparatus according to the invention, in terms of their advantages, modes of operation and preferred variants, attention is directed to the foregoing description of the respective properties of the corresponding development of the method.

DESCRIPTION OF THE DRAWINGS

The invention is described hereinafter by means of specific embodiments and test results with reference to the drawings in which.

DETAILED DESCRIPTION

Figure 1:
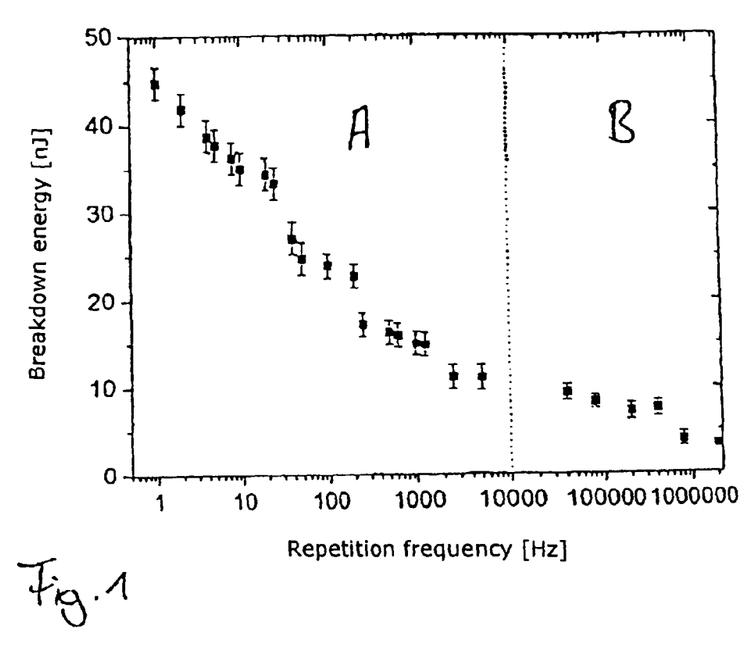
FIG. 1 shows a diagram illustrating the relationship between the pulse energy to be introduced for material division and the laser pulse repetition frequency.

Referring to FIG. 1 it can be seen from this diagram which in the region A was determined with a laser pulse duration of 150 fs, a wavelength of 780 nm and an aperture of 0.6 and in the region B with a laser pulse duration of about 15 fs, a wavelength of 800 nm and an aperture of 0.5, that, with a laser pulse repetition frequency of 1 Hertz, an energy of about 45 nJ is required to achieve material division. That required level of energy falls with an increasing laser pulse repetition frequency and reaches a value of below 5 nJ at a laser pulse repetition frequency of 1 MHz.

Figure 2:
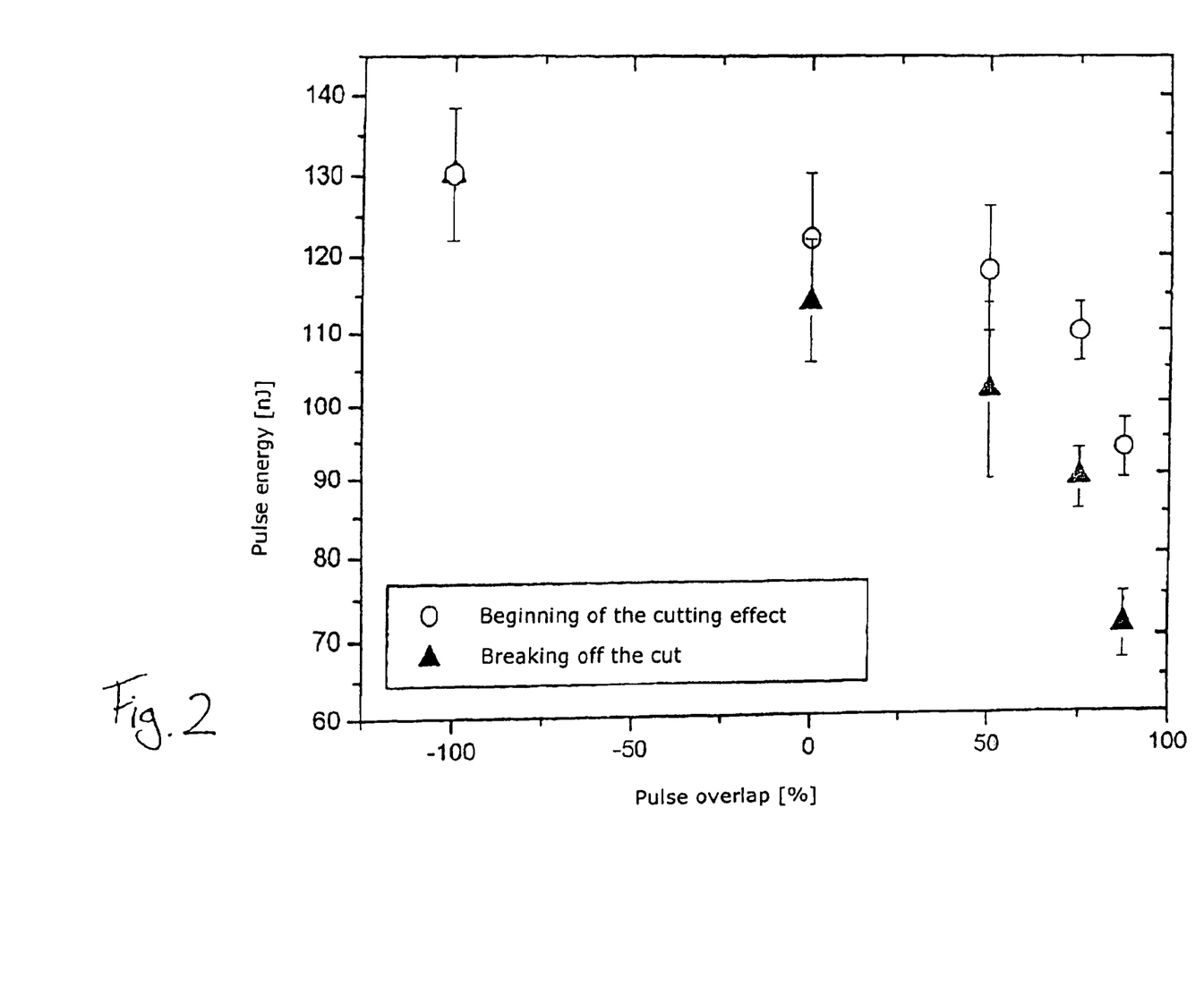
FIG. 2 shows a diagram illustrating the relationship between the laser pulse energy required for the beginning of material division and the laser pulse energy required at least for continuing with material division, with a laser pulse overlap in the range of −100% to +100%.

FIG. 2 shows the dependency of the laser pulse energy required for beginning a material division operation ('beginning of the cut') and the laser pulse energy at least required for continuing with the material division ('breaking off the cut') with the laser pulse overlap in the range of −100% to +100%. In that respect a negative pulse overlap signifies that between two adjacent pulses there remains a non-irradiated region of material which, with a −100% pulse overlap, for example precisely corresponds to the focus diameter.

It can be seen that, with adequate spacing in respect of the individual pulses from each other (negative pulse overlap) the beginning and the break-off of the cutting effect occur with the same pulse energy, that is to say there is no mutual influencing of the pulses. The greater the pulse overlap that is adopted however, the correspondingly lower is on the one hand the pulse energy which is required for beginning the cut and the pulse energy at which the cut is broken off. In addition the pulse energy which is required for beginning the cut and the pulse energy at which the cut is broken off are correspondingly further apart, the higher the degree of pulse overlap. Consequently, division can be initially effected with a correspondingly lower level of pulse energy and the cutting operation can be continued with a corresponding lower level of pulse energy, the greater the degree of pulse overlap that is adopted.

Figure 3:
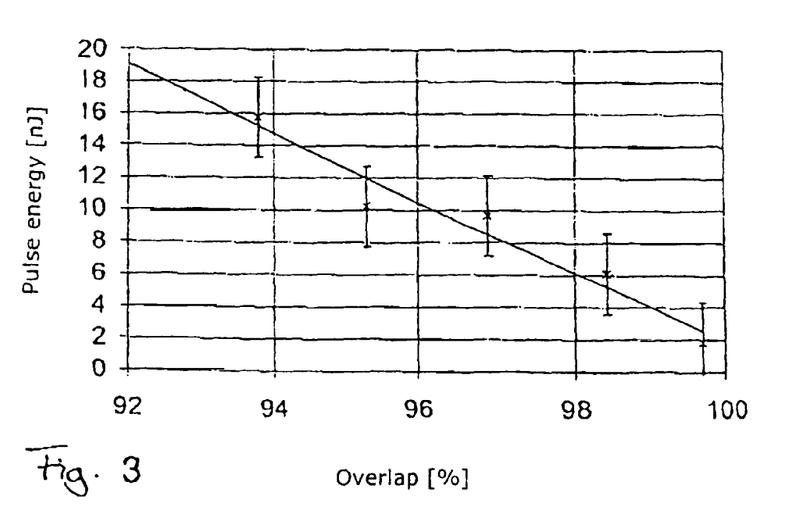
FIG. 3 shows a diagram illustrating the relationship between a laser pulse energy required for material division, with the laser pulse overlap in the range of 92% to 100%.

FIG. 3 shows the measurement results for the cutting operation with high levels of pulse overlap. The diagram plots the results of five series of measurements with different degrees of overlap and a compensating straight line through those series of measurements. It can be seen that, with an overlap of 92%, the method must be operated with an individual laser pulse energy of about 19 nJ. That required level of individual laser pulse energy falls with an increasing degree of overlap and, with an overlap of about 99.5%, reaches a value of just 2 nJ.

Figure 4:
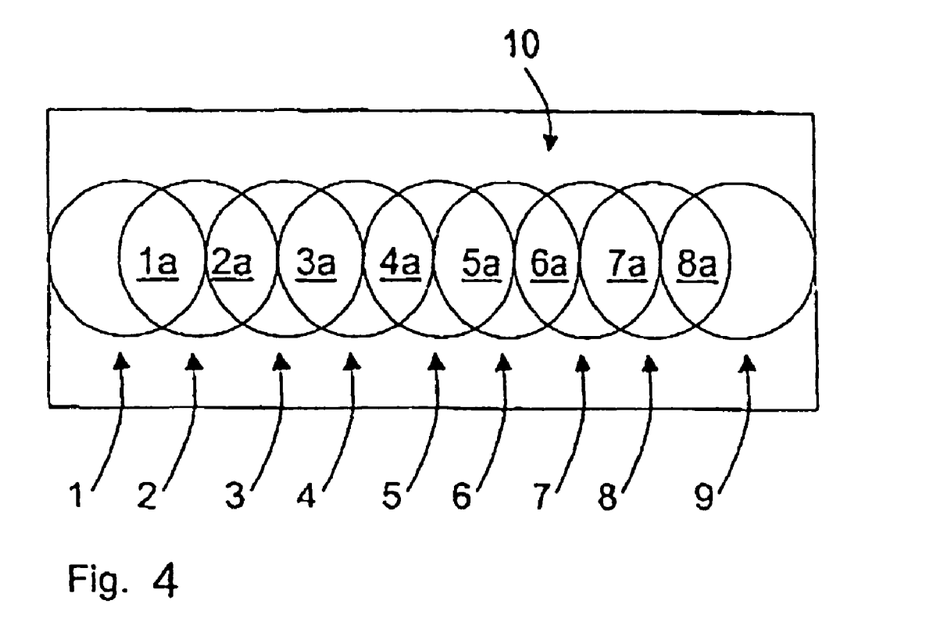
FIG. 4 shows a diagrammatic representation of line material division with a laser pulse overlap of 50%.

Referring to FIG. 4, shown therein is a material 10 to be divided and a succession of individual laser pulses 1-9 which serve to divide that material. The individual laser pulses are diagrammatically shown in the configuration of their focus area. The individual laser pulses 1-9 are applied to the material in succession in respect of time from left to right. In that case the laser pulses each overlap in the regions 1-8a. In the procedure of the method as illustrated in FIG. 4 the laser pulse repetition frequency, the advance speed and the focus diameter are so set that there is an overlap of 50%, that is to say the laser pulses 1 and 2 overlap in the region 1a, the laser pulses 2 and 3 overlap in the region 2a and so forth. In that way, each region along the line of cut is irradiated by two laser pulses.

Figure 5:
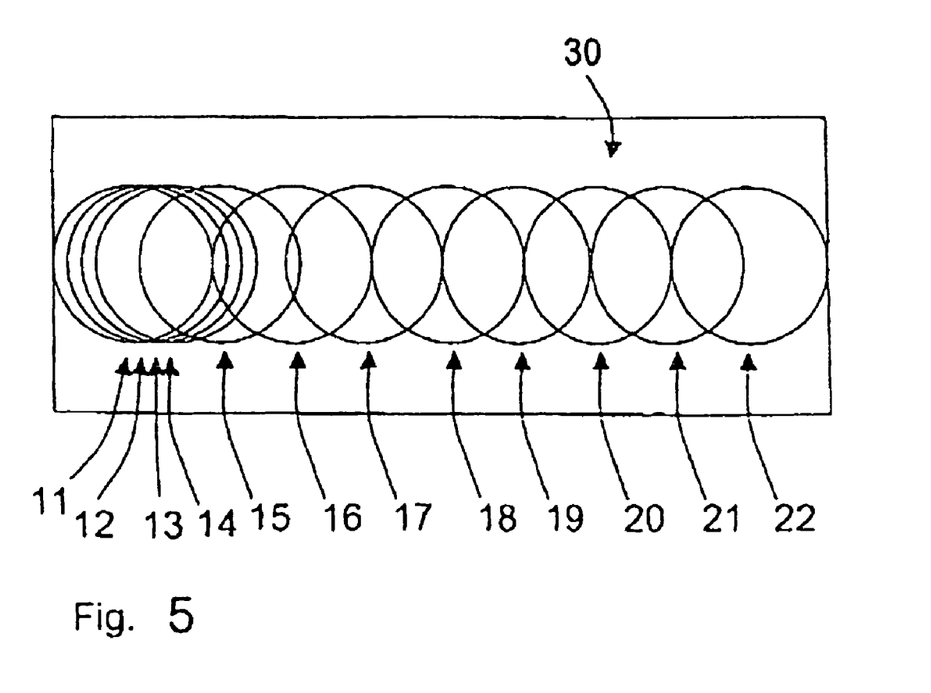
FIG. 5 shows a diagrammatic representation of line material division with a variable laser pulse overlap in the start region and in the further course of the division operation.

Referring to FIG. 5, shown therein is a succession of laser pulses 11-22 serving to divide a block of material 30.

The laser pulses 11-22 are applied in a rising sequence from left to right. It can be seen that the laser pulses 11-14 involve a greater degree of overlap than the following laser pulses 15-22. That serves to introduce, in the left-hand start region of the division operation, a higher level of total energy which is sufficient for initial division, than in the further course of the procedure towards the right along the division line where only a lower level of total energy is required for the division region in order to continue with initial division.

The accumulation of laser pulses 11-14 shown in FIG. 5 can be achieved for example by selecting an increased laser pulse repetition frequency in that start region or by setting a reduced advance speed in that start region.

The invention claimed is:

1. A method of effecting a refractive surgical treatment of corneal tissue in an animal or human by a process that comprises:
    irradiating corneal tissue at a location in a division region with a succession of spatially overlapping, successive laser pulses for achieving material division of said corneal tissue, wherein each laser pulse exhibits an energy that is less than the laser pulse energy which is required for producing material division with an isolated laser pulse but which irradiates said corneal tissue with a sufficient total energy to effect material division when irradiated with a plurality of successive laser pulses that are successively introduced in the division region in a spatially overlapping orientation.

2. A method according to claim 1 characterized in that the laser pulse energy is reduced by reducing the laser pulse intensity and/or the laser pulse duration.

3. A method according to claim 1 wherein the irradiated region is spatially overlapped by at least two laser pulses, which occur in succession in respect of time, of the succession of laser pulses.

4. A method according to claim 3 wherein the irradiated region is spatially overlapped by at least two laser pulses, which occur in succession in respect of time, of the succession of laser pulses in the range of between 10% and 100%.

5. A method according to claim 1 wherein the laser pulse energy, the laser pulse intensity, the dimensions of the focus area, the laser pulse duration of an individual laser pulse, the laser pulse repetition frequency of the succession of laser pulses and/or the advance speed between the laser beam and the material to be processed is preset in dependence on properties of said material region.

6. A method according to claim 1 wherein the laser pulse repetition frequency of the succession of laser pulses is so high that, within a material-specific period of time of the material to be divided, at least two laser pulses are delivered on to the material to be divided.

7. A method according to claim 6 characterized in that the laser pulse repetition frequency is higher than 10 Hz.

8. A method according to claim 6 wherein the laser pulse energy, the laser pulse intensity, the dimensions of the focus area, the laser pulse duration of an individual laser pulse, the laser pulse repetition frequency of the succession of laser pulses and/or the advance speed between the laser beam and the material to be processed is varied during the processing operation.

9. A method according to claim 8 characterized in that at a first laser pulse repetition frequency a first laser pulse energy is set and at a second laser pulse repetition frequency which is higher than the first last pulse repetition frequency a second laser pulse energy is set, which is lower than the first laser pulse energy.

10. A method according to claim 9 characterized in that the laser pulse repetition frequency is set automatically in dependence on the laser pulse energy, or the laser pulse energy is set automatically in dependence on the laser pulse repetition frequency, the laser pulse energy and/or the laser pulse repetition frequency are set automatically in dependence on the advance speed, or the laser pulse repetition frequency, the laser pulse energy and/or the advance speed are set automatically in dependence on at least one material property of the material to be divided.

11. A method according to claim 1, characterized in that in the start region of the dividing operation, the total energy introduced at a location of the material to be processed is higher than in a region in the further course of the dividing operation.

12. A method according to claim 1 wherein the start region the laser pulse energy and/or the laser pulse repetition frequency is higher and/or the advance speed between the laser beam and the material to be processed is lower, than in the further course of the division operation.

13. A method according to claim 1 wherein the laser pulse intensity is higher and/or the laser pulse duration of an individual laser pulse is longer in the start region of the division operation than in a region in the further course of the division operation.

14. A method according to claim 1 wherein the laser pulse duration is less than 10 picoseconds.

15. A method according to claim 1 wherein the laser beam is focused, preferably with an optical system having a numerical aperture which is at least so great that material division is achieved under the surface of a semitransparent or completely transparent material without material regions which are above or beneath the division region being damaged.

16. A method according to claim 15 wherein the division operation is observed and if the division performance drops off the total energy introduced is increased by altering at least one of the laser pulse energy, the laser pulse intensity, the dimensions of the focus area, the laser pulse duration of an individual laser pulse, the laser pulse repetition frequency of the succession of laser pulses, and the advance speed between the laser beam and the material to be processed.

17. A method according to claim 1 wherein a first cut for opening up a cornea is effected by irradiating a region of the cornea with the succession of laser pulses.

18. A method according to claim 17 further comprising a second cut for removing a lens-shaped piece of tissue from the cornea is effected by irradiating a region of the cornea with the succession of laser pulses.

* * * * *